United States Patent [19]

Klose et al.

[11] Patent Number: 4,690,899
[45] Date of Patent: Sep. 1, 1987

[54] PROCESS AND DEVICE FOR CARRYING OUT ANALYTICAL DETERMINATIONS

[75] Inventors: Sigmar Klose, Berg; Manfred Pasch, Tutzing; Helmut Schlumberger, Polling; Wolfgang Kleemann, Tutzing; Friedhelm Vieth, Haunshofen, all of Fed. Rep. of Germany

[73] Assignee: Boehringer Mannheim GmbH, Mannheim, Fed. Rep. of Germany

[21] Appl. No.: 751,368

[22] Filed: Jul. 2, 1985

[30] Foreign Application Priority Data

Jul. 6, 1984 [DE] Fed. Rep. of Germany ....... 3425008

[51] Int. Cl.⁴ .................. G01N 21/07; G01N 21/11
[52] U.S. Cl. .......................... 436/45; 422/72; 422/102; 436/165; 436/169
[58] Field of Search .............. 422/58, 64, 72, 102; 436/45, 165, 169, 178

[56] References Cited

U.S. PATENT DOCUMENTS

| | | |
|---|---|---|
| 3,899,296 | 8/1975 | Marlen et al. .......................... 422/72 |
| 4,279,862 | 7/1981 | Bretaudiere et al. ................. 422/72 |
| 4,284,602 | 8/1981 | Kelton et al. .......................... 422/72 |
| 4,469,793 | 9/1984 | Guigan .................................. 422/72 |

Primary Examiner—Barry S. Richman
Assistant Examiner—C. M. Delahunty
Attorney, Agent, or Firm—Felfe & Lynch

[57] ABSTRACT

In a process for carrying out an analytical determination by mixing and incubating a sample liquid with at least one dry reagent which is soluble therein to form a reaction mixture liquid and measuring a parameter in the reaction mixture liquid, the sample liquid is first transported along a transport path to the soluble dry reagent and the resulting reaction mixture liquid then further transported along the transport path. The further transporting of the reaction mixture liquid along the transport path is under the influence of a force-change cycle in which centrifugal force and a further force alternately predominate to determine the direction of the further transporting along the transport path. At least one further liquid is transported on another path, part of which is separate from and part of which is common with the transport path, by the force-change cycle in such a manner that at least two of the liquids pass through the common part of the transport path chronologically separated.

8 Claims, 6 Drawing Figures

PROCESS AND DEVICE FOR CARRYING OUT ANALYTICAL DETERMINATIONS

The present invention is concerned with a process for carrying out an analytical determination using centrifugal force and a device suitable for carrying out this process.

A known process for carrying out an analytical determination first transports a sample liquid along a transport path from a point of introduction to a dry reagent which at least partially dissolves therein, and then further transports the liquid along the transport path to a measurement point. The transporting takes place by two different forces, an interfacial force acting on the solution as the first force which, and a variable centrifugal or pressure force for regulating the transport velocity or direction depending upon which of the two forces, is greater or smaller (see Federal Republic of Germany Patent Specification No. 31 34 611). Such a process is especially suitable for a centrifugal analysis apparatus having on its rotor one or more insert elements with the soluble dry reagent so that only the sample solution has to be added to the elements.

Because of the simplicity and low possibilities of error in the case of such a process, there is a need to be able to carry out as many different analytical determinations as possible, especially within the scope of the determination of clinical parameters in the investigation of body fluids. Recently, numerous complicated analytical methods have been developed, for example on an immunological basis, in which heterogeneous phases occur. Thus, for example, many methods of radioimmunoassay (RIA) or of enzyme immunoassay (EIA) are based on the presence of a reaction component in insoluble form which enters into a chemical exchange reaction with a soluble phase. A typical example of this is the so-called ELISA processes in which one of the components of the immune reaction is bound to the solid phase, whereas the other component or components of the immune reaction is or are present in the dissolved phase. However, such processes cannot be so arranged or can only be so arranged with difficulty so that, without any kind of manipulations, they can be carried out on automatic analyzers and especially on centrifugal analyzers since, as a general rule, several different liquids are needed or wash liquids and the like must be handled.

It is an object of the present invention further to develop a process of the initially mentioned kind in such a manner that it can be applied to methods which take place chronologically in several steps and is also suitable for carrying out such complicated methods of analysis, especially of methods of analysis which require heterogeneous phases, for example immunological determinations.

Thus, according to the present invention, there is provided a process for carrying out an analytical determination by mixing and incubating a sample liquid with at least one dry reagent which is soluble therein to form a reaction mixture liquid and measuring a parameter in the reaction mixture. The sample liquid is first transported along a transport path to the soluble dry reagent for at least partially dissolving the latter thereinto to form the reaction mixture liquid. The reaction mixture liquid is then further transported along the transport path under the influence of a force-change cycle in which centrifugal force and a further force alternately predominate to determine the direction of the further transporting. At least one further liquid is transported on another path, part of which is separate from and part of which is common with the transport path, by the force-change cycle in such a manner that at least two of the liquids pass through the common part of the transport path chronologically separated.

According to the present invention, without further external measures after initiating the process, it is possible, solely by the force-change cycles, to allow several chronologically separated procedures to take place at one reaction point.

The present invention is based upon the recognition that centrifugal force and a further force, especially a capillary force, can be allowed to act simultaneously on several liquid transport paths and the transport paths can thereby be adapted to the force-change cycles in such a manner that a common part of the transport path is passed through by different liquids chronologically separated.

In a preferred embodiment of the process according to the present invention, at least one of the transport paths is constructed in such a manner that the liquid transported therein, at each force change cycle, only passes along a part of the path separated from the path of the other liquid. If both liquid transport paths are so constructed, one of the separate liquid transport paths requires more force-change cycles in order to reach the transport path common for at least two of the liquids than does the other transport path.

The force-change cycle in the case of the process according to the present invention consists of a first force in the form of a centrifugal force and of a second force, preferably in the form of a capillary force, one of which alternatingly predominates the other.

Instead of a capillary force, within the scope of the present invention, there can also be used another suitable force, for example a pressure force, an electrical field or the force of gravity.

As a rule, a force-change cycle can even be carried out by the change of one of these forces, thus by an alternating increase or decrease of this force in such a manner that it exceeds the second force or is overcome by it. For example, it is sufficient alternatingly to increase and to decrease the centrifugal force by increasing or decreasing the speed of rotation of the centrifuge rotor. However, it is also possible correspondingly to vary the second force or so to change the centrifugal force and the second force that they alternatingly preponderate. As the second force, within the scope of the present invention, there can also be provided more than one force competing with the centrifugal force. For example, besides the centrifugal force as first force, a capillary force and a gravitational force and/or an electric field can represent the second force.

The transparent paths for the sample liquid and the further liquid used within the scope of the present invention are, within the scope of the present invention, so constructed that, in the case of each force-change cycle, a definite path length is passed by the liquid within the transport path. For example, one liquid can be transported with one or two force-change cycles up to a common part of the transport path of all liquids, whereas the further liquid, for example the second or third liquid etc., requires two or more force-change cycles in order to get to the same common point of the transport path. On the common part of the transport path, as a rule there is then arranged the reactant present in the solid phase. In the case of the latter, it can be, for example, a component of an immune reaction, i.e. an antigen, a hapten, an antibody fragment or the like.

Therefore, in an especially preferred embodiment of the present invention, in the part of the transport path common for the various liquids there is provided at least one solid reactive insoluble material, for example an immune reagent, on which at least two reactions are allowed to take place chronologically separated from one another in that it is first contacted with that solution which requires less force-change cycles up to reaching this insoluble reactive material and only thereafter is or are the further liquid or liquids brought into contact therewith.

If, for example, the process according to the present invention is used in order to determine a substance active as antigen or hapten present in the sample liquid according to the ELISA principle, then the sample solution can first be transported for dissolving the dry reagent, which contains a known amount of the substance to be determined in enzyme-marked form, the mixture obtained, which contains an unknown amount of unmarked substance and a known amount of marked substance, is then further passed to the common part of the transport path where the immunological partner of the substance to be determined is present in insoluble phase. There then takes place a competitive binding of marked and unmarked substance to the solid phase in dependence upon the amount ratio of the two to one another. In a subsequent force-change cycle, the sample liquid is then further transported and passed, for example, into a waste chamber. During this time, the further liquid, for example a reagent or wash liquid, after passing through a larger number of force-change cycles than the sample solution, preferably with dividing up into individual portions, also reaches the common part of the transport path, there washes the insoluble phase, for which purpose one or more individual portions can be used, thereby reacts with the marking enzyme which is bound to the insoluble phase, with colour formation and is subsequently wholly or partly further transported to the measurement point and there measured, whereas the portions only used for the washing are previously passed to the waste chamber and thus are removed from the further course of the reaction.

If desired, instead of a portioning of the second liquid, a third liquid can also be transported through a further transport path according to the same principle to the common part of the transport path, there bringing about a colour reaction and finally transported to the measurement point. In this case, it is possible to use the second liquid only as wash liquid and the third liquid only as a reagent liquid, which makes possible the quantitative determination of the marking enzyme which is used as component of the dry reagent dissolved by the sample solution for the marking of the known amount of substance to be determined. Thus, for example, if the marking enzyme used is peroxidase, which is frequently employed in the ELISA process, then the third liquid is preferably a peroxidasedetermination reagent which, in the presence of the enzyme, develops an amount of colored material proportional to the amount of the enzyme and, thus, also inversely proportional to the amount of the sought substance, which colored material is measured at the measurement point, for example in a cuvette.

In an analogous manner, other embodiments of the ELISA principle can also be carried out with the process according to the present invention.

In another embodiment of the process according to the present invention, for example for the determination of a hapten or antigen in a sample liquid, an antibody-enzyme conjugate is provided in the soluble dry reagent, which conjugate, after dissolving by the sample solution, leads to the formation of a dissolved complex of hapten or antigen and conjugate and excess free conjugate. Under the influence of the force-change cycle, this mixture is then passed to the common part of the transport path in which further hapten or antigen is present in insoluble phase. Excess conjugate still present is there retained, whereas the liquid containing the hapten-conjugate complex or antigen-conjugate complex is further transported to a dry reagent for the determination of the enzyme bound in the conjugate, dissolves this and, in a further force-change cycle, is finally transported to the measurement cuvette in which the enzyme reagent is measured. As second liquid, in this case there can be used a wash liquid which is either introduced directly into the chamber which contains the hapten or antigen bound in insoluble phase or is introduced into a separate chamber preceding the solid phase chamber. A pre-washing of the insoluble phase is hereby achieved, which washes out hapten or antigen liberated during storage before the actual sample liquid comes into contact therewith. Therefore, in the case of this embodiment, the common part of the liquid paths can be the same as the total path which the second liquid passes.

The process according to the present invention permits numerous variants which can be seen from the following description, in conjunction with the accompanying drawings.

In the drawings, there is schematically illustrated on an enlarged scale a disposable insert element intended for single use, which insert element is suitable for carrying out the process according to the present invention. In the drawings.

Figure 1:
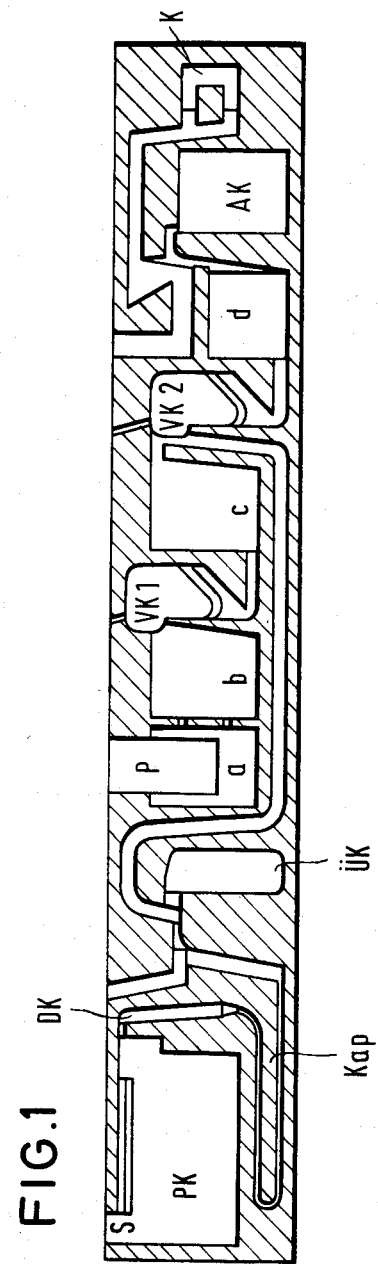
FIG. 1 is a perspective schematic illustration of a first embodiment of an insert element.

FIG. 1 shows an insert element with two liquid paths separated from one another. The first liquid path consists of a sample chamber (P) connected with a chamber (a) which is possibly filled with an absorbent material, for example a fleece. Chamber (a) is connected with chamber (b) which also can be filled with fleece. The fleeces are normally not needed but extend the field of use, especially for reagents with components which tend to have undesired reactions with one another. A second path for a further liquid leads into a valve chamber (VK1) and from there, via a chamber (c), which is again filled with an absorbent material, to the beginning of a common part of the liquid paths, a valve chamber (VK2). For simple reactions, chambers (c) and (VK1) can be omitted.

The second liquid path begins with a pump/substrate chamber (PK), leads via a dosing chamber (DK) and a capillary (Kap) to an overflow chamber (ÜK) and from there directly to the valve chamber (VK2). The common part of both of the paths leads from the valve chamber (VK2) to a chamber (d) in which is present, for example, a solid phase-bound reaction component, from there to a collection chamber (AK) and to a cuvette (K). Pressure equilibration bores prevent the formation of an air pillow disturbing the liquid transport.

This insert element is suitable for transporting liquid in a controlled manner exclusively by variation of the centrifugal force, whereas in the capillaries (run-offs from VK1 and VK2, as well as Kap) in each case a constant capillary force is present.

The process according to the present invention can be carried out in this insert element in the following way:

By means of a suitable centrifuging programme with alternating increase and decrease of the speed of rotation, on the one hand, a sample introduced into the chamber (P) is brought, via chamber (a), (b), (VK1), (c) and (VK2), into the chamber (d) which acts as a separating column with a component of an immune reaction insolubly fixed on an absorbent filling therein. For example, the absorbent filling consists of a cellulose fleece on which an immune reaction component is covalently fixed. On the other hand, by means of the centrifuging programme, the liquid introduced into the pump chamber (PK) is separated in the dosing chamber into several individual, comparatively small and equal substrate volumes, the first of which is collected in the overflow chamber (ÜK). In the case of continuation of the centrifuging programme, the chamber (d) is emptied, the overflow chamber (ÜK) is caused to overflow further, successive substrate volumes of solution and, via the valve chamber (VK2), individual substrate volumes of the solution are then brought into the chamber (d) which, before the arrival of the next substrate volume of the solution, are, in each case, centrifuged out. After several such wash procedures, a portion of the substrate liquid remains for a definite reaction time in the chamber (d) and reacts there with carrier-bound marking enzyme with the development of a colour. The remaining amount of the sample, as well as the individual wash volumes centrifuged out of (d), almost completely fill the collection chamber (AK) constructed as overflow chamber so that the substrate liquid portion finally reacting on (d) flows, for the greater part, past (AK) into the cuvette (K) and is there measured in known manner. The volume of the collection chamber (AK) is adjusted to the volume of the sample solution, dosing chamber and overflow chamber, taking into account the volume of the cuvette (K) and the desired number of wash portions, depending upon the volume of the substrate liquid.

In the following, the functions of the various parts are described in detail:

DOSING CHAMBER (DK) AND CAPILLARY (KAP)

The pump chamber (PK) for the substrate liquid contains fleece material which is able to absorb the total amount of the substrate liquid. The fleece forms a plurality of interconnected small hollow spaces which provide a resistance to centrifugal transport of the substrate liquid. Thus, only in the case of centrifuging at a high enough speed of rotation, is the substrate liquid forced from the pump chamber fleece into the dosing chamber (DK) to fill it completely. The capillary (Kap) which turns back under the pump chamber (PK) from the dosing chamber (DK) is, under this centrifugal force, only partly filled in its upper half.

In the case of then reducing the speed of rotation to stopping, the substrate liquid is absorbed back into the fleece in the pump chamber (PK). At the entry to the dosing chamber (DK), this separates the substrate liquid and, only then, as a result on the force of gravity of the liquid in the dosing chamber (DK) and the sucking power of the capillary (Kap), does it come to fill the capillary (Kap) completely from the dosing chamber (DK). In the case of subsequent centrifuging with a low speed of rotation, the capillary acts as a siphon and sucks empty the dosing chamber (DK).

Another embodiment of the overflow chamber (ÜK) (FIG. 3) permits the sucking empty of dosing chamber (DK) and capillary (Kap) in a stationary state by contact of the fleece in the overflow chamber (ÜK) with the run-off from capillary (Kap).

Only in the case of resumed high speed rotation does the fleece in the pump chamber (PK) allow a new filling of the dosing chamber (DK) and partial filling of the capillary (Kap). This procedure is repeated several times up to the desired portioning of the total substrate liquid volume in the pump chamber (PK).

OVERFLOW CHAMBERS (UK AND AK)

As already mentioned, the collection chamber (AK) also functions as an overflow chamber. The entry into these overflow chambers is so constructed that the liquid is passed into these under the prevailing centrifugal force and the air present therein can be completely expelled. Preferably the AK contains fleece material to fix the liquid.

As soon as the chamber is completely filled, the further liquid flows past it.

The overflow chamber (ÜK) makes it possible, in spite of sample and substrate liquids in the two separate chambers (PK and P), to transport the sample liquid, by a suitable centrifuging program, via the two valve chambers (VK1 and VK2) to the chamber (d), while the substrate liquid is held back in the overflow chamber (ÜK).

Figure 3:
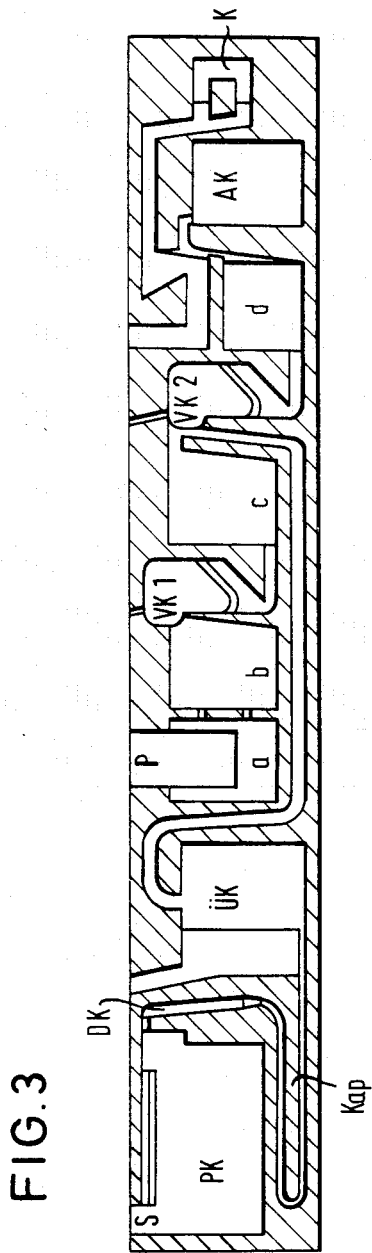
FIG. 3 is a schematic illustration of a third embodiment of an insert element.

An alternative construction of the overflow chamber (ÜK) is shown in FIG. 3. Here, a definite volume of liquid is also held back but all dosed portions flow through the chamber. The advantage of this chamber lies in the holding back of the throughflowing liquid in the case of low speeds of rotation.

Furthermore, by means of the collection chamber (AK), the possibility is provided to collect the remainder of the sample liquid and the individual wash volumes and only to pass into the cuvette (K) the substrate solution reacting on the separating column (d).

Figure 2:
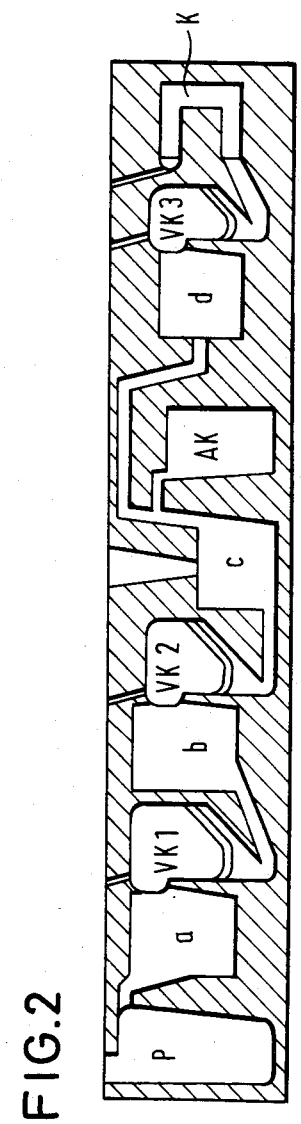
FIG. 2 is a schematic illustration of a second embodiment of an insert element.

FIG. 2 shows a further insert element with two liquid paths in which the second liquid path represents completely a part of the longer first liquid path. In the case of this embodiment, in the chamber (c) there is present on the solid phase, for example in the form of a cellulose fleece, insolubly bound hapten or antigen. The chamber (c) has an opening through which a liquid can be pipetted in. Therefore, the second liquid path consists of the chamber (c), which is connected with a collection chamber (AK). The first liquid path begins with the sample chamber (P), goes from (P) further to chamber (a), in which is present a dry reagent on a fleece, from there to the valve chamber (VK1), in which the reaction between sample and reagent dissolved out from chamber (a) can take place. From valve chamber (VK1), the first liquid path continues to the chamber (b), which can contain, for example, enzyme-marked antibody or fragments thereof. They are also dissolved out by the sample liquid and react in the following valve chamber (VK2). Thereafter, they pass into chamber (c) and thus into the common part of the first and second paths. The common part of the first and second paths leads to the chamber (d), in which is present a dry reagent, and thereafter follows valve chamber (VK3), as well as a connecting path leading from there to the measurement cuvette (K).

In operation, with this embodiment of the insert element, the process takes place as follows:

Wash liquid pipetted into the matrix chamber (c) is, during the first centrifuging, centrifuged into the collection chamber (AK). Hapten molecules, the binding of which to the matrix has broken during storage, are hereby removed from the matrix.

At the same time, sample liquid is introduced into the sample chamber (P). During the first centrifuging, the sample liquid overflows the chamber (a), thereby dissolves the reagents there present and passes into the valve chamber (VK1) where the reaction takes place. In the case of simultaneous reactions, fields (a) and (VK1) can be omitted, the application of the total reagent for the pre-reaction on to field (b) and incubation in (VK2) being sufficient.

In the case of reduction of the centrifugal force, the capillary force preponderates and the sample solution is sucked out of (VK1) and passes into chamber (b). Enzyme-marked antibodies or preferably anti-body fragments are there dissolved out. Upon increasing the centrifugal force, the liquid passes into the valve chamber (VK2) and can there react so long as the centrifugal force is maintained. Upon reduction of the centrifugal force (stopping), the sample is sucked out by the capillary force and passes into chamber (c), i.e. into the common path of both liquids. The reaction can there proceed until, in a further step, by increasing the centrifugal force, the liquid is centrifuged out of (c) and partly passes into (AK) until it is filled and partly passes directly to chamber (d). There, still under the influence of the centrifugal force, the enzyme detection reagent is dissolved out and immediately further transported into valve chamber (VK3), where the colour-forming reaction begins or takes place. Upon reduction of the centrifugal force, due to the capillary force, the solution is sucked out of (VK3) and, in the case of again increasing the centrifugal force, is transported into the cuvette (K) and measured.

Further subjects of the present invention are the preferred embodiments of rotor insert elements for centrifugal analysers illustrated in FIGS. 1 to 3, which are suitable for carrying out the process according to the present invention.

A rotor insert element for centrifugal analysers according to the present invention, consisting of a formed body, a sample application chamber, which is connected with a plurality of reagent zones, each of which contains an absorbent material impregnated with a particular reagent, at least one mixing valve chamber and a measurement chamber which together form a sample liquid transport path which runs radially from the inside to the outside when the insert element is fixed on to a rotor, is characterised by at least one further chamber for the reception of a liquid and a transport path which leads from this chamber to the measurement chamber and is at least partly identical with the sample liquid transport path.

A preferred embodiment of such an insert element is characterised in that the sample liquid transport path leads from the sample application chamber (P) via one or more chambers (a), possibly (b), (c) or more, filled with absorbent material and containing dry reagents, and a first valve chamber (VK1) arranged between the chambers, for example (b) and (c), to a second valve chamber (VK2) and from this, via a chamber (d) provided with carrier-fixed immune reactants, formed as a separating column, and via a collection chamber (AK) to the measurement chamber (K) and, for the reception of a further liquid, a pump/substrate chamber (PK) is provided which, via a dosing device consisting of a dosing chamber (DK) and capillary (Kap) and an overflow chamber (ÜK), is connected with the second valve chamber (VK2).

An alternative embodiment of the insert element according to the present invention is characterised in that the sample liquid transport path passes from the sample application chamber (P) via the chambers (a) and (b), filled with absorbent material containing dry reagents, as well as chamber (c), which is constructed as a separating column with carrier-fixed immune reactants, between which valve chambers (VK1 and VK2) are arranged, past reception chamber (AK) to the chamber (d) containing dry reagent and filled with absorbent material and further, if desired via a third valve chamber (VK3) to the measurement chamber (K), the chamber (c) having an opening to the outside through which a further liquid can be introduced which passes via (c) into the collection chamber (AK).

The valve chambers and the measurement chamber of the insert element according to the present invention preferably have aeration canals.

The function of the insert elements according to the present invention are explained in more detail by the following Examples within the scope of carrying out the process according to the present invention:

EXAMPLE 1

Determination of TSH as antigen, with the use of an insert element according to FIG. 1.

Provision of the chambers of the rotor insert element:
Substrate solution:
0.9 NaCl
Na HEPES, 70 mM, pH 7.25
boric acid, 5 mM
magnesium hydroxide, 0.5 mM
bovine serum albumin (BSA) 0.3%
chlorophenol red galactoside, 50 mM (substrate)
  PK: 0.2% Tween 20
fleece to a total thickness of 3.5 mm.
  UK: fleece to a total thickness of 2 mm.
a:
  2 fleeces each of 0.7 mm. thickness
  Na HEPES, 50 mM, pH 7.25 (37° C.)
  Tween 20, 0.1%
  lactose, 3%
c:
  1 fleece, 1 mm. thickness anti-TSH monoclonal antibody Fab fragment coupled to $\beta$-galactosidase, 200 mU (Fab-E)
  monoclonal antibody against TSH, 250 ng.
  HEPES, 200 mM, pH 7.25
  magnesium aspartate, 20 mM
  saccharose, 6%
  BSA, 1%

Tween 20, 0.1% d:
- 2 fleeces, 0.7 mm. thickness
- loaded with 5 mg. sheep IgG-anti-mouse-Fcγ (antibody against anti-TSH)
- washed with:
  - NaPO$_4$, 10 mM, pH 6.5
  - NaCl, 154 mM
  - BSA, 1%.

AK: 4 fleeces with a total thickness of 3.5 mm.

Liquid pipettings

280 μl. of substrate solution are pipetted into the pump/substrate chamber. 40 μl. of sample are pipetted through an opening on the upper rim directly on to the zone (a). In this case, the sample is undiluted.

Carrying out of the reaction

By means of a suitable reaction programme, in which high speeds of rotation alternate with stopping, sample and substrate are now conveyed in the direction of the separating matrix and cuvette. In the following, centrifuging means a high speed of rotation and intermediate stages with a lower speed of rotation serve for the more sensitive control of the liquid transport but do not change the principle function. The substrate/wash solution is divided up by the dosing capillary (DK) into equally large portions. Use is made of a disposable insert element according to FIG. 3.

1st centrifuging

Sample and sample buffer are centrifuged into VK1, the first portion is in dosing chamber DK.

1st stopping

Sample and sample buffer to chamber c and dissolve anti-TSH and Fab-E (conjugate). The first portion of substrate solution passes into overflow chamber ÜK.

2nd centrifuging

TSH, anti-TSH and Fab-E pass into VK2, centrifuging for 5 minutes, homogeneous mixing taking place.

The first portion of substrate solution is held back in ÜK and the second portion of substrate solution passes into dosing chamber DK.

2nd stopping

On the sample side, the liquid is transported to zone d, i.e. the complexes formed in the preceding reaction now reach the matrix; there follows a stopping for 5 minutes, during which time the complexes are bound to the matrix. Antibodies against anti-TSH are firmly bound to the matrix. Non-complexed anti-TSH is also bound. At the end of the reaction, uncomplexed Fab-E is present in the solution in the matrix. The second portion of substrate solution passes into ÜK.

3rd centrifuging

The liquid in chamber d is centrifuged into the collection chamber (AK) and with it the excess of Fab-E. The second portion of substrate is retained in ÜK. The third portion of substrate is present in dosing chamber DK.

3rd stopping

The third portion of substrate is conveyed to ÜK.

4th centrifuging

Portion 4 to DK; portion 3 to VK2.

4th stopping

Portion 4 to ÜK; portion 3 to zone d. The first wash portion is present on the matrix.

5th centrifuging

Portion 5 to DK; portion 4 to VK2; portion 3 to AK.

5th stopping

Portion 5 to ÜK; portion 4 to d; the second wash portion on the matrix.

6th centrifuging

Portion 6 to DK; portion 5 to VK2; portion 4 to AK.

6th stopping

Portion 6 to ÜK; portion 5 to d; third wash portion on the matrix.

7th centrifuging

Portion 7 to DK; portion 6 to VK2; portion 5 to AK.

7th stopping

Portion 7 to ÜK; portion 6 to d; fourth wash portion on the matrix.

8th centrifuging

Portion 8 to DK; portion 7 to VK2; portion 6 to AK.

8th stopping

Portion 8 to ÜK; portion 7 to d; detection portion on the matrix. In 5 minutes reaction, the substrate is split by the enzyme bound to the matrix, i.e. an amount of enzyme which, due to the complex formation, is proportional to the amount of TSH used, and the colour to be measured is formed.

9th centrifuging

The liquid coming from the matrix completely fills the AK with a first aliquot and the remainder is conveyed to the cuvette. In the cuvette there takes place the measurement of the colour formed at 578 nm.

The described course of the reaction is suitable for all polyvalent antigens. The only things which have to be changed are the antibodies against the antigen to be determined present on fleece c, i.e. anti-Ag and Fab-E. There are used three phases, each of 5 minutes, namely:
homogeneous mixing in VK2
matrix binding of the resultant complex on d,
colour development by the enzyme bound on the matrix on d.

Between the matrix reaction and the colour development, there are several wash steps in order to remove excess enzyme.

Figure 4:
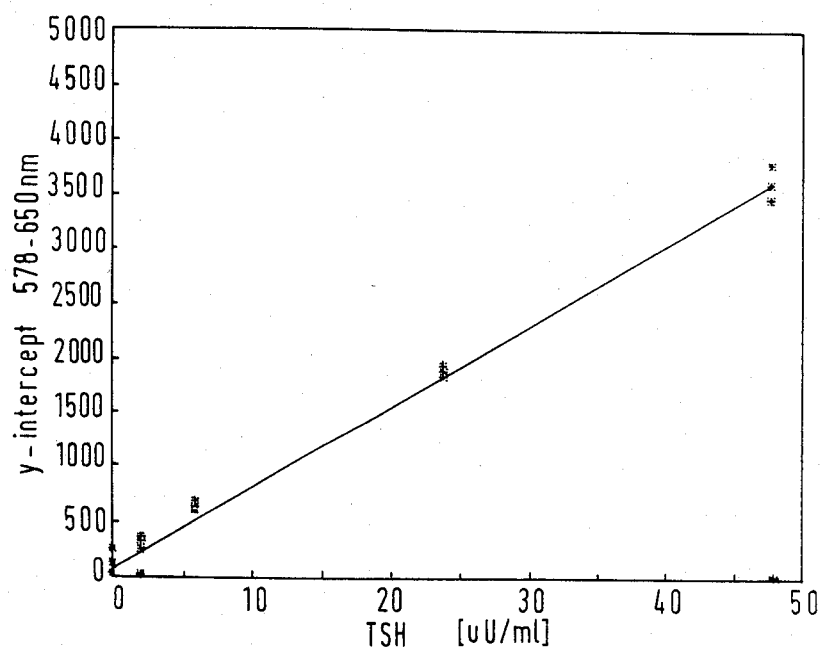
FIGS. 4, 5 and 6 are calibration curves obtained with the use of insert elements according to the present invention.

Due to the proportionality of the amount of enzyme bound on the matrix to the concentration of the analyte, there are obtained linear calibration curves. A calibration curve for TSH is illustrated in FIG. 4 of the accompanying drawings.

If β-galactosidase is not used as the marking enzyme, in the substrate chamber the chlorophenol red galactoside is replaced by an appropriate substrate suitable for the other enzyme used. These substrates are known to the expert.

EXAMPLE 2

Determination of HCG

The process is analogous to that of Example 1 but as conjugate on fleece there is used a Fab fragment-enzyme compound of a monoclonal antibody (MAB) against HCG. Furthermore, there is used a second MAB against HCG.

EXAMPLE 3

Determination of AFP

The process is as in Example 1, the antibodies used on fleece c being directed against AFP. Because of the high concentration of AFP in the serum, the sample is pre-diluted in a ratio of 1:10 with physiological saline.

EXAMPLE 4

Determination of T3 as an example of a hapten, i.e. of a monovalent antigen, with the use of an insert element according to FIG. 2.

Provision of the insert element:

a:
  2 fleeces of buffer, 1 fleece of dissolving reagent, each 0.5 mm. thick
  Na HEPES, 125 mM, pH 7.25
  Tween 20, 0.25%
  ANS 0.06% (ANS=anilinonaphthalene-sulphonic acid)
  Tween 20, 0.01% b:
  2 empty fleeces, 1 conjugate fleece, each of 0.5 mm. thickness
  anti-T3 monoclonal antibody Fab fragment bound to $\beta$-galactosidase 1.6 mU (Fab-E)
  Na HEPES, 100 mM, pH 7.25
  polyoxygelatine 1%
  magnesium aspartate, 5 mM c:
  separation matrix, 2 fleeces, each 0.7 mm. thick T3, insolubly bound to the matrix fleece AK:
  1 fleece of 1 mm. thickness d:
  1 fleece of 0.5 mm. thickness
  Na HEPES, 100 mM, pH 7.25
  boric acid, 5 mM
  chlorophenol red galactoside 18 mM

Liquid pipettings

5 μl. of sample solution are pipetted into the sample application chamber P, followed by 50 μl. of diluent (physiological saline). The mixing of the components takes place by the pipetting procedure. 40 μl. of diluent are pipetted on to zone c.

Carrying out of the reaction

The centrifuging programme is identical to the programme according to Example 1 up to and including the 3rd stopping. Thereafter, there follows directly the measurement of the reaction at the measurement speed of rotation.

1st centrifuging

The liquid pipetted on to the matrix (c) is centrifuged into the reception chamber (AK). By means of this washing procedure of the matrix, hapten molecules, the binding of which to the matrix has broken during storage, are removed. These molecules would otherwise act like sample and falsify the result. The sample liquid simultaneously flows over the zone a, thereby dissolves the reagents there present and a pre-reaction can take place in the valve chamber VK1. The dissolving reaction, in which ANS dissolves the T3 from the binding with the binding proteins (preponderantly TBG), does not have to be complete since a further reaction in VK2 is here possible.

1st stopping

The sample passes to zone b and here the Fab-Enzyme conjugate is dissolved off.

2nd centrifuging

The sample is conveyed to VK2. This centrifuging is maintained for 5 minutes. The T3 from the sample hereby reacts with the Fab-enzyme conjugate (Fab-E) to give the complex T3.Fab-E.

2nd stopping

The sample passes to fleece c. Excess Fab-E here binds to the matrix via the matrix-bound T3. This reaction lasts for 5 minutes.

3rd centrifuging

The first part of the liquid completely fills the reception chamber, the greater part is centrifuged over fleece d into VK3. The substrate is hereby dissolved out from d.

3rd stopping

The reacting solution leaves VK3.

Measurement centrifuging

The solution is transported into the cuvette where the reaction takes place and is monitored absorption-photometrically at 578 nm. The conjugate molecules which had bound T3 from the sample could pass the matrix and there is now an amount of enzyme in the cuvette corresponding to the concentration of T3. The measured increase of colour per unit time is, therefore, a measure of the concentration of T3 in the sample.

Figure 5:
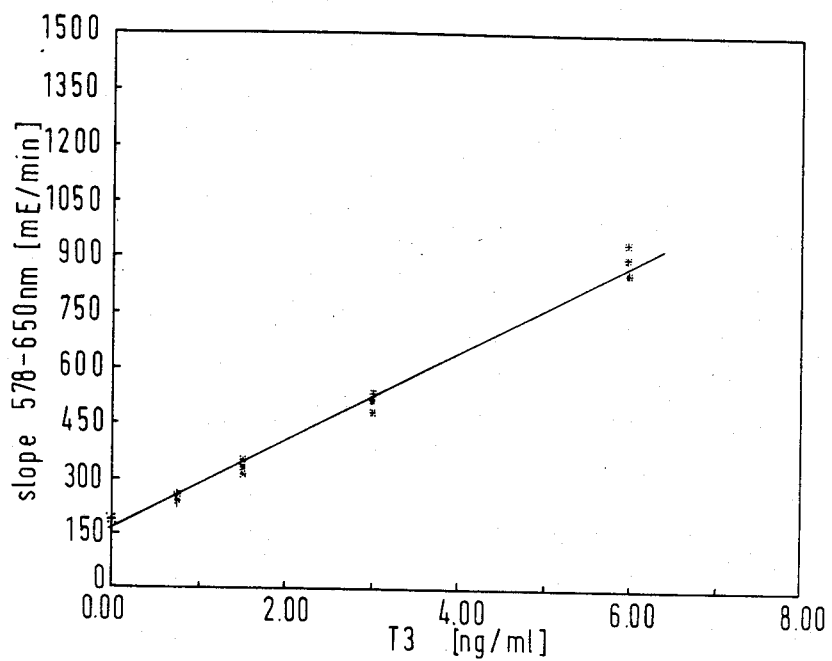

Because of the proportionality between enzyme and analyte, linear calibration curves are obtained. This is shown by FIG. 5 of the accompanying drawings.

EXAMPLE 5

Determination of digoxin

Figure 6:
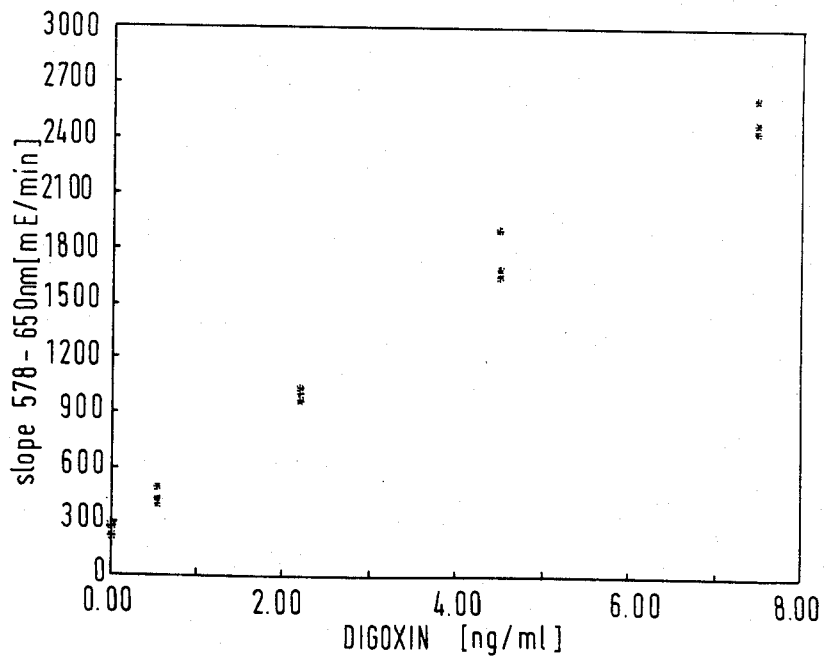

The process is analogous to that of Example 4 but for the conjugate there are used Fab fragments from an antibody against digoxin. In this case, the matrix consists of digoxin bound to the solid phase. A calibration curve obtained in this manner is shown in FIG. 6 of the accompanying drawings.

We claim:

1. In a process for carrying out an analytical determination by mixing and incubating a sample liquid with at least one dry reagent soluble therein to form a reaction mixture liquid and measuring a parameter in the reaction mixture liquid, the improvement comprising:
  transporting a sample liquid along a first transport path to a dry reagent positioned in said first transport path and which is soluble in said sample liquid for at least partially dissolving of the latter in the sample liquid to form a reaction mixture liquid;
  then further transporting the reaction mixture liquid along the first transport path under the influence of a force-change cycle in which centrifugal force and a further force alternately predominate to determine the direction of the further transporting along the first transport path; and
  transporting at least one further liquid along a second path, an initial part of which is separate from and a downstream part of which is common with the first transport path, by the force-change cycle simultaneously with the further transporting of the reaction mixture liquid in such a manner that at least the reaction mixture liquid and one of said further liquids pass through the common part of the transport path chronologically separated.

2. Process according to claim 1, and further comprising having at least one insoluble material in the common part of the first and second transport paths which reacts with the reaction mixture liquid and, differently, with the further liquid, the two reactions taking place chronologically separated from one another by the chronological separation of the transporting of the liquids along the common part of the first and second transport paths, the reaction mixture liquid reaching the common part of the first and second transport paths and, thus, the insoluble material therein for its reaction therewith first, and the further liquid thereafter.

3. Process according to claim 2, wherein the soluble, dry reagent is a marked, immunologically-active material which is bindable with a substance to be determined and the insoluble reactive material is a material immunologically bindable with the marked, immunologically-active material.

4. Process according to claim 1, wherein at least one of the first and second transport paths is so constructed that the liquid transported therein passes only a portion of that part of said at least one of the first and second transport paths which is not common to both said first and second transport paths during each force-change cycle.

5. Process according to claim 4 wherein in both said first and second transport paths only a portion of that part of each of said first and second transport paths which is not common to both said first and second transport paths in passed by its respective liquid during each force change cycle and wherein one of said first and second transport paths requires more force change cycles to move its respective liquid from an initial portion of said one of said first and second transport paths to said common part of said first and second transport paths than is required by the other of said first and second transport paths.

6. Process according to claim 5, and further comprising having at least one insoluble material in the common part of the first and second transport paths which reacts with the reaction mixture liquid and, differently, with the further liquid, the two reactions taking place chronologically separated from one another by the chronological separation of the transporting of the liquids along the common part of the first and second transport paths, the reaction mixture liquid reaching the common part of the first and second transport paths and, thus, the insoluble material therein for its reaction therewith first, and the further liquid thereafter.

7. Process according to claim 6, wherein the soluble, dry reagent is a marked, immunologically-active material which is bindable with a substance to be determined and the insoluble reactive material is a material immunologically bindable with the marked, immunologically-active material.

8. In a process for carrying out an analytical determination by mixing and incubating a sample liquid with at least one dry reagent soluble therein to form a reaction mixture liquid, the improvement comprising: transporting a sample liquid along a first transport path to a dry reagent positioned in said first transport path and which is soluble in said sample liquid for at least partially dissolving of the latter in the sample liquid to form a reaction mixture liquid; then further transporting the reaction mixture liquid along the first transport path under the influence of a force-change cycle in which centrifugal force and a further force alternatively predominate to determine the direction of the further transporting along the first transport path; and transporting at least two further liquids along a second and a third path, an initial part of each of said second and third paths being separate from and a downstream part of each of said second and third paths being common with the first transport path, by the force-change cycle simultaneously with the further transporting of the reaction mixture liquid in such a manner that the reaction mixture liquid and at least one of said at least two further liquids pass through the common part of the transport path chronologically separated.

* * * * *